United States Patent
Powell

Patent Number: 5,906,644
Date of Patent: *May 25, 1999

[54] ADJUSTABLE MODULAR ORTHOPEDIC IMPLANT

[76] Inventor: Douglas Hunter Powell, 44910 S. El Macero Dr., El Macero, Calif. 95618

[*] Notice: This patent is subject to a terminal disclaimer.

[21] Appl. No.: 08/885,674

[22] Filed: Jun. 30, 1997

Related U.S. Application Data

[63] Continuation-in-part of application No. 08/706,406, Aug. 30, 1996.

[51] Int. Cl.⁶ .................................................... A61F 2/30
[52] U.S. Cl. ................................. 623/23; 623/16; 623/20
[58] Field of Search ................................ 623/16, 18, 19, 623/20, 22, 23

[56] References Cited

U.S. PATENT DOCUMENTS

| | | |
|---|---|---|
| 3,102,536 | 9/1963 | Rose . |
| 3,846,846 | 11/1974 | Fischer ...................................... 623/23 |
| 4,011,602 | 3/1977 | Rybicki et al. . |
| 4,012,795 | 3/1977 | Dorre et al. . |
| 4,459,708 | 7/1984 | Buttazzoni . |
| 4,502,160 | 3/1985 | Moore et al. ............................... 623/18 |
| 4,520,511 | 6/1985 | Gianezio et al. ........................... 623/23 |
| 4,608,055 | 8/1986 | Morrey . |
| 4,676,979 | 6/1987 | Schellenberg et al. . |
| 4,693,724 | 9/1987 | Rhenter et al. . |
| 4,846,839 | 7/1989 | Noiles . |
| 4,876,917 | 10/1989 | Aiki et al. . |
| 4,878,917 | 11/1989 | Kranz et al. . |
| 4,919,678 | 4/1990 | Kranz . |
| 4,995,883 | 2/1991 | Demane et al. ........................... 623/23 |
| 5,002,578 | 3/1991 | Luman ....................................... 623/23 |
| 5,002,581 | 3/1991 | Paxson et al. . |
| 5,035,712 | 7/1991 | Hoffman ................................ 623/23 X |
| 5,080,685 | 1/1992 | Bolesky et al. . |
| 5,108,452 | 4/1992 | Fallin . |
| 5,181,928 | 1/1993 | Bolesky et al. . |
| 5,201,882 | 4/1993 | Paxson . |
| 5,286,260 | 2/1994 | Bolesky et al. . |
| 5,370,706 | 12/1994 | Bolesky et al. . |
| 5,397,360 | 3/1995 | Cohen et al. . |
| 5,405,398 | 4/1995 | Buford, III et al. . |
| 5,489,311 | 2/1996 | Cipolletti ................................... 623/20 |
| 5,507,830 | 4/1996 | DeMane et al. ........................... 623/23 |
| 5,531,792 | 7/1996 | Huene . |
| 5,569,263 | 10/1996 | Hein ...................................... 623/23 X |
| 5,653,765 | 8/1997 | McTighe et al. ...................... 623/18 X |
| 5,658,349 | 8/1997 | Brooks et al. ............................. 623/23 |

FOREIGN PATENT DOCUMENTS

| | | |
|---|---|---|
| 0 634 154 A1 | 1/1995 | European Pat. Off. . |
| 0 729 732 A2 | 9/1996 | European Pat. Off. . |
| 2 297 257 | 7/1996 | United Kingdom . |
| WO 97 20525 | 6/1997 | WIPO . |

*Primary Examiner*—David J. Isabella
*Attorney, Agent, or Firm*—Hall & Kerr

[57] ABSTRACT

An implantable modular orthopedic prosthesis, preferably for hip, knee or shoulder arthroplasty, is disclosed which consists of three components. A first component has an elongated stem with a free end, configured to be situated within the intramedullary canal of a patient's bone, and an opposite end having an articulating portion such as a Morse-tapered member. A second component has another articulating portion which can also be a corresponding tapered member that is matingly engageable with the articulating portion of the first component. A third component has a body with a linearly-extruded channel through which the articulating portions are adjustably received, wherein at least one of the first and second components is radially-expandable to pressure lock against an internal surface of the channel in a selected position and arrest the first, second and third components together as the articulating portions are fully engaged with one another.

39 Claims, 12 Drawing Sheets

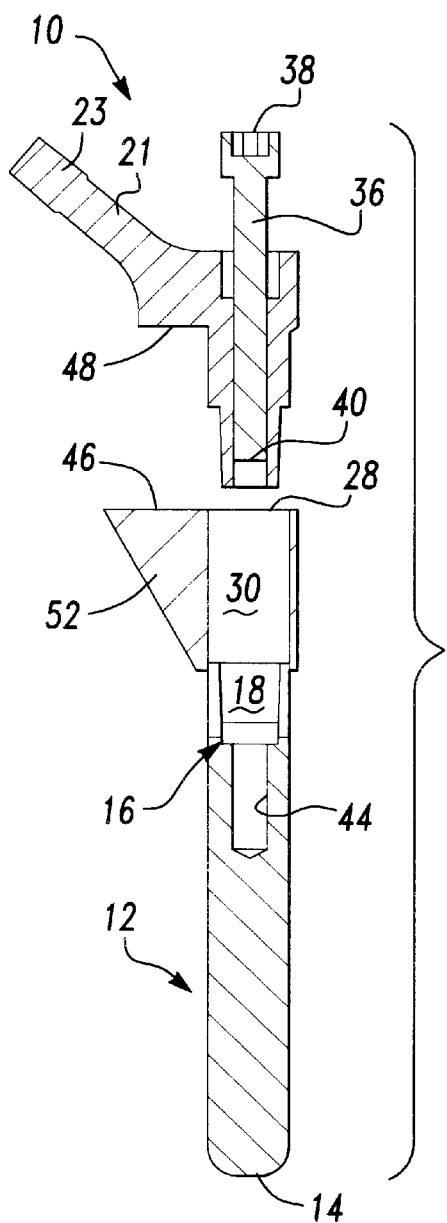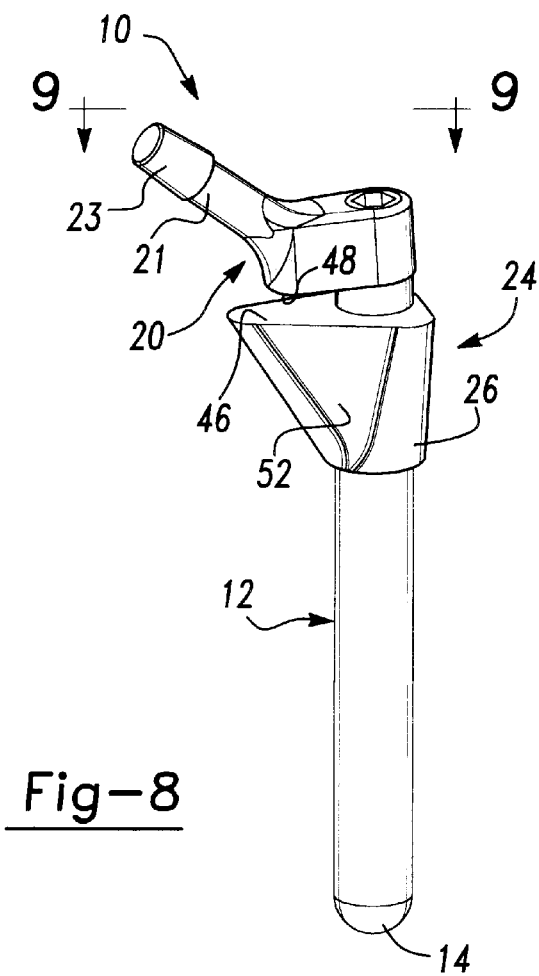

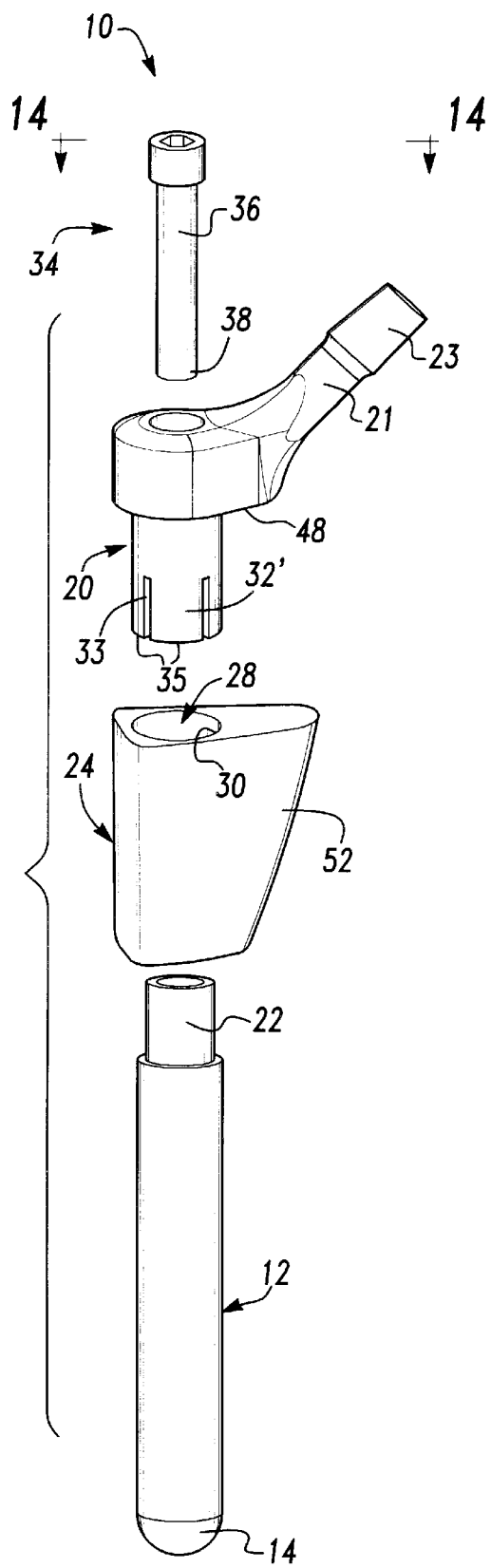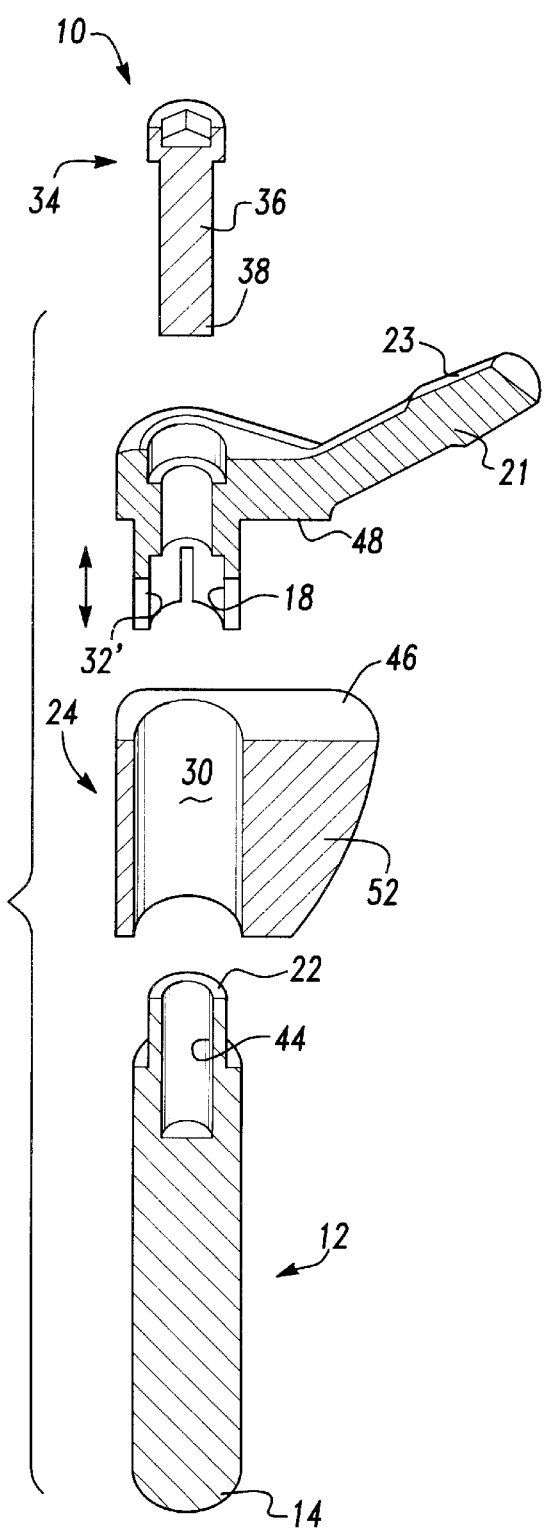
Fig-13
Fig-14

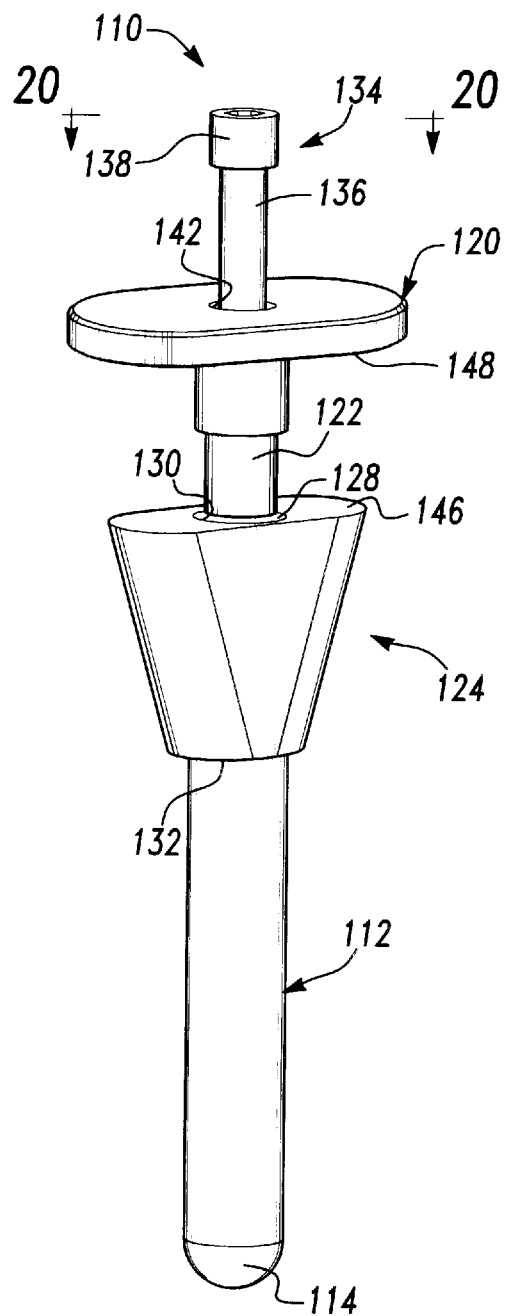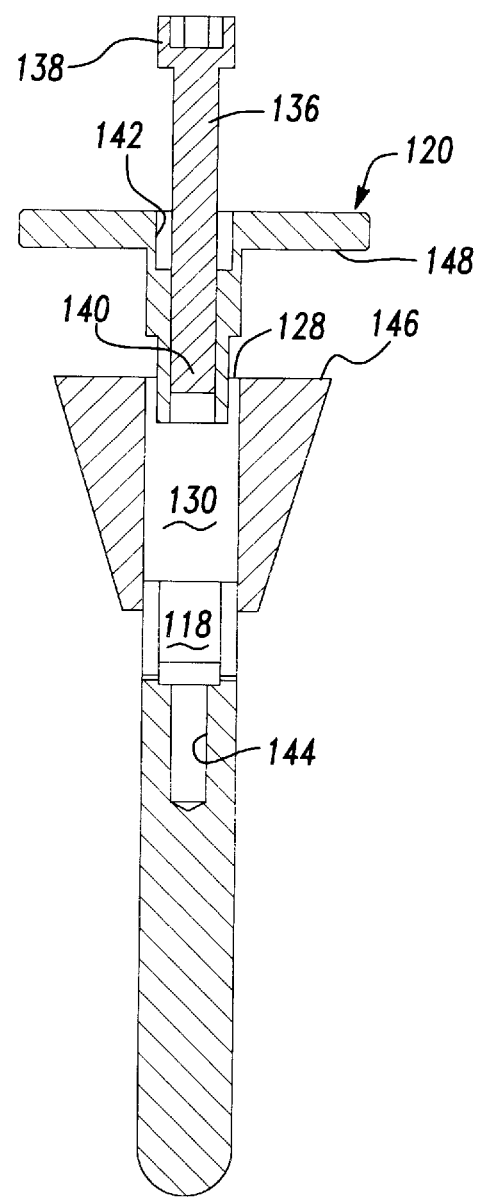
Fig-19
Fig-20

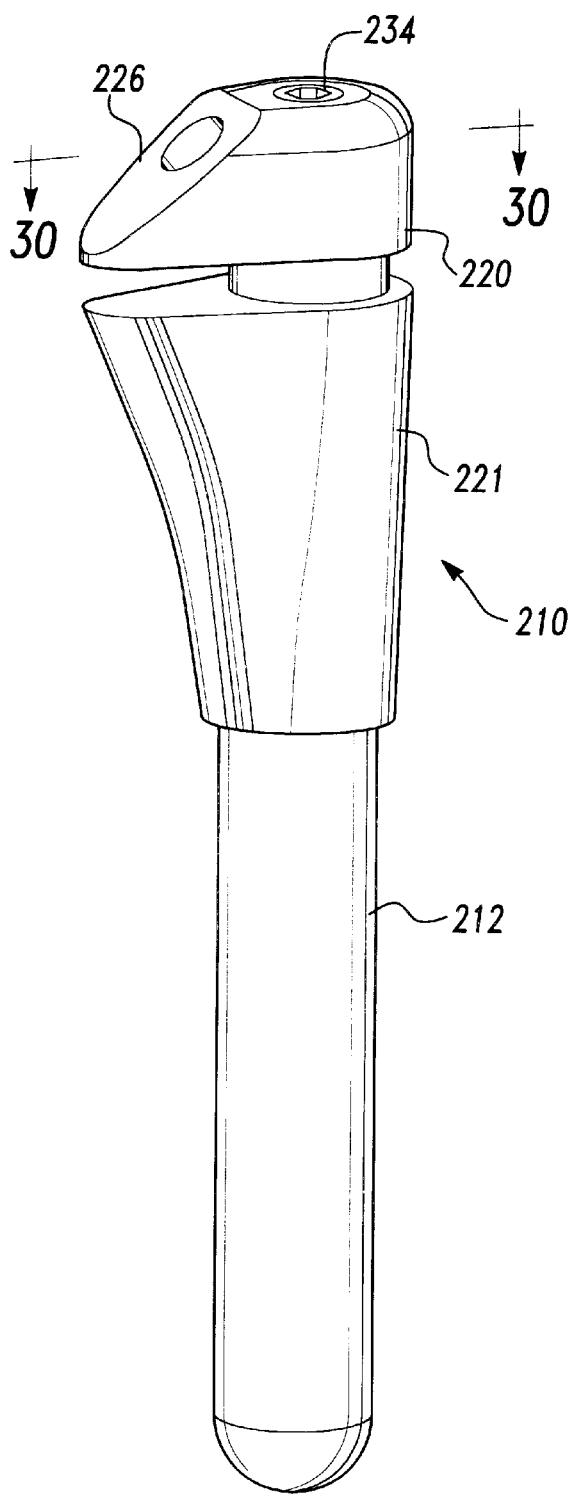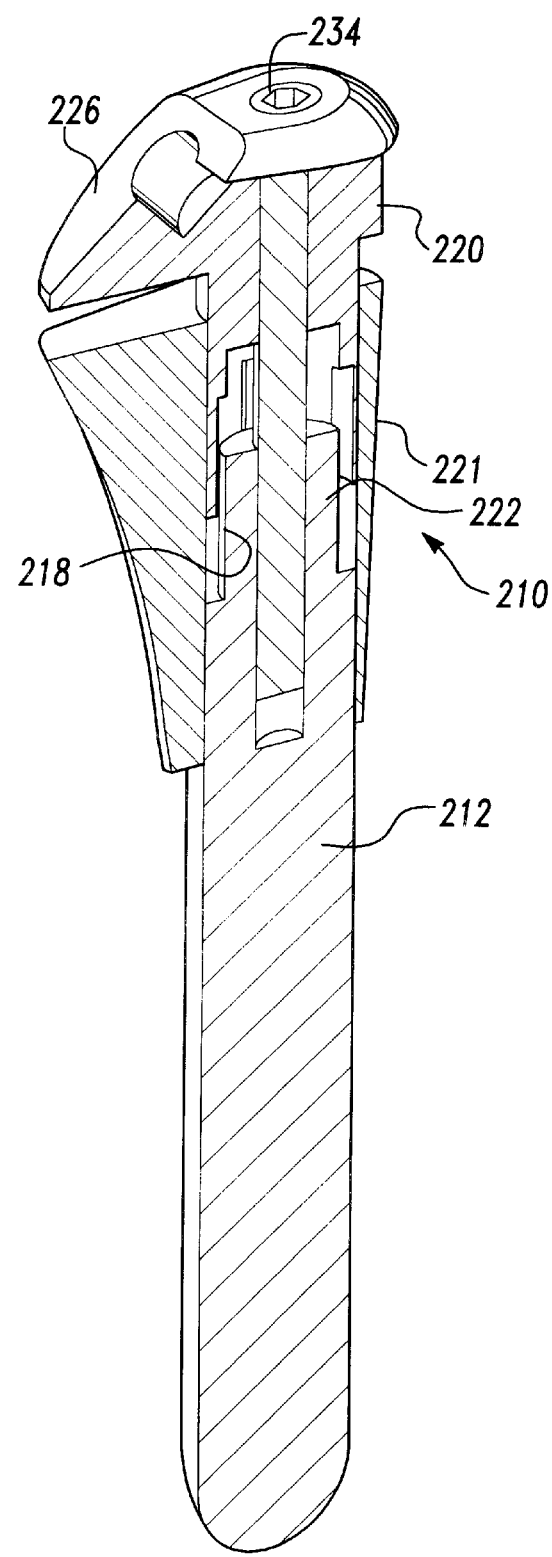
Fig-29
Fig-30

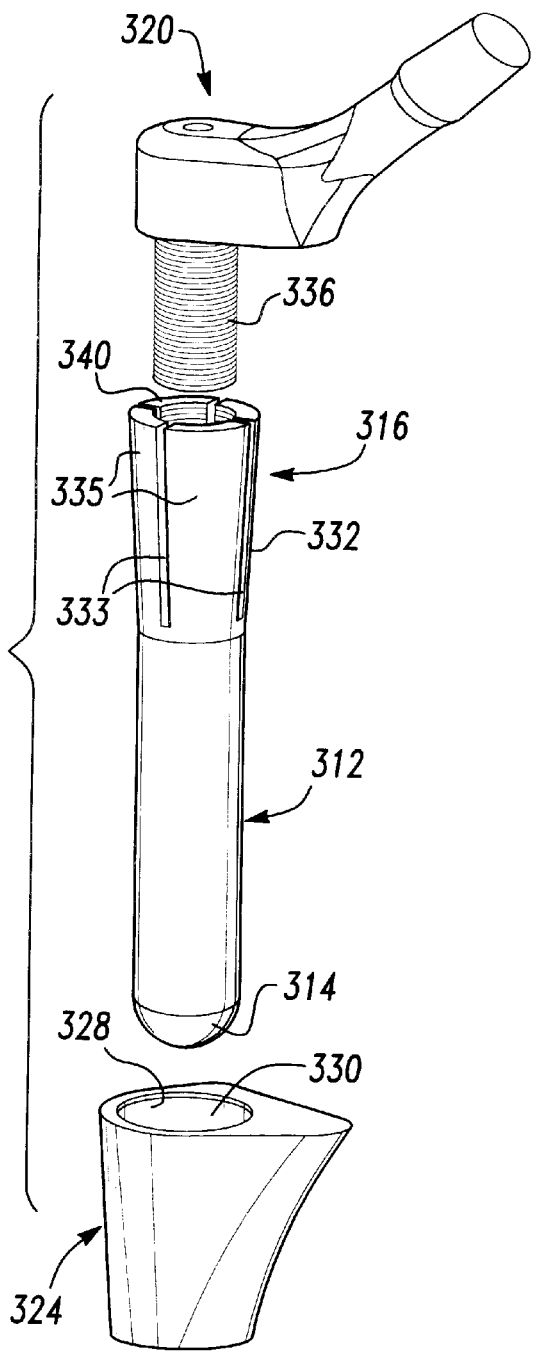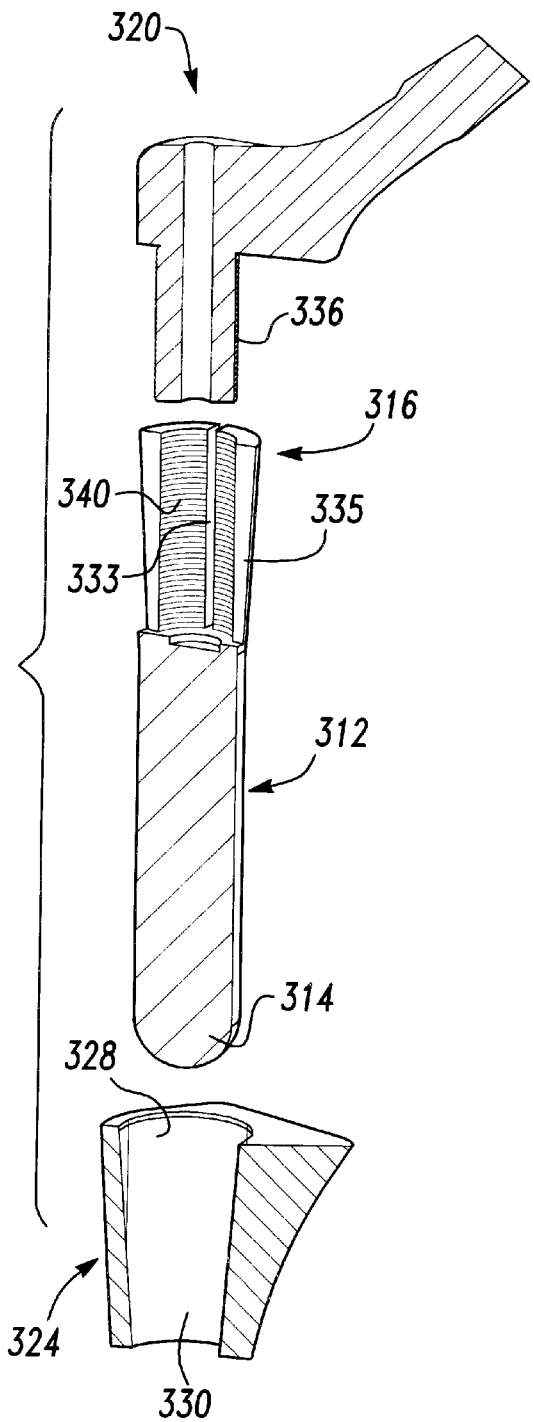
Fig-31
Fig-32

ADJUSTABLE MODULAR ORTHOPEDIC IMPLANT

This is a continuation-in-part of copending application Ser. No. 08/706,406 filed on Aug. 30, 1996.

BACKGROUND OF THE INVENTION

1. Field of the Invention

This invention relates generally to modular implantable orthopedic prostheses, and particularly those which are adjustable in size to fit a given patient's needs.

2. Description of the Prior Art

Various prostheses have heretofore been designed to replace one or both components of a ball and socket hip joint. Generally the ball portion is connected to an arm composed of a neck and a stem or shaft which stem or shaft is embedded in the intramedullary canal of the proximal femur for hip reconstruction. Such prostheses are often formed with an integral stem and neck portion. Often a removable ball or head element is positioned on the proximal end of the neck. See, for example, U.S. Pat. Nos. 4,012,795 or 4,459,708.

Recently, the assembly of modular structures together from a number of replaceable parts available in a variety of sizes have been used. With such prostheses, it is possible to replace either the head portion or trochanteral portion of the prostheses, or both, without removal of the stem from the bone cavity during implantation. U.S. Pat. Nos. 4,608,055, 4,676,979 and 4,693,724 are all illustrative of such approaches. The latter patent also discloses the possibility that the angle at which the neck protrudes from the proximal end of the femur may be adjusted without removal of the stem by pivoting the neck on the end of the implanted stem.

These prior art devices, however, failed to provide a means for varying the angle between the axis of the trochanteral module and the axis of the stem so that the actual angulation (sometimes referred to as anteversion) or slope of the proximal end of the femur might be duplicated by adjustment of said angle. U.S. Pat. Nos. 5,002,581 and 5,201,882 to Paxson et al. filled such a need, by providing a modular device and instrumentation for implanting such device with the proper anteversion to match that of a patent's anatomy. The components of Paxson's device are secured together using complementary standard tapered connections (for example, a Morse taper may be used).

Other modular hip prostheses have been proposed, which are said to address various objects of design and use, among these the achievement of a "custom fit". For example, U.S. Pat. No. 4,995,883 to Demane et al. discusses using transitional sections of variable length between the several components of the device, secured together via combinations of a locking screw and tapered fittings. U.S. Pat. No. 5,002,578 to Luman discloses a modular hip having a neck inserted via a shouldered member to a unitary trochanteral/stem component, with a locking screw running through its shoulder into the trochanteral/stem component to secure the two components together. U.S. Pat. Nos. 5,080,685, 5,181,928, 5,286,260 and 5,370,706, all to Bolesky, each provide a modular prosthesis kit, capable of interoperative assembly by the surgeon, who chooses the proper size of components prior to implantation. U.S. Pat. No. 5,108,452 to Fallin shows a modular hip having extension sleeves to adjust the length between the ball and neck, as well as additional pads to increase the cross-sectional shape of the prosthesis body. U.S. Pat. No. 4,876,917 to Kranz et al., discloses a modular hip prosthesis having a stem with a distal tip that is radially expandable to anchor the stem against the medullary canal wall.

U.S. Pat. No. 4,846,839 to Noiles discloses a modular prosthesis design, alternatively adaptable to either total hip or knee arthroplasty, which presents a stepped contour interface with the patient's bone. The components of this design are connected via conventional tapers. A further type of device used for the fixation of modular prosthesis components is sold by H. D. Holmes under the registered trademark Spiralock®, consisting of a clamping screw which fastens a standard taper connection together, e.g., connecting either the tibial tray or femoral component of a total knee joint to its respective stem. A further example of the use of such locking screws in a modular hip prosthesis is found in U.S. Pat. No. 5,397,360 to Cohen.

U.S. Pat. No. 5,405,398 to Buford, III, et al. discloses a knee prosthesis with a femoral component having a pin including a split ring which expands to keep the pin in place. U.S. Pat. Nos. 5,531,792 to Huene and 4,011,602 to Rybicki et al. each show bone fixation plugs having radially expanding members to apply compressive forces against the surrounding bone and promote in growth of the tissue into the member. Neither of these contemplate an improved mechanism for connecting the components of modular orthopedic implants of the type used in large or small total joint arthroplasty.

The modular knee and hip joint prostheses, described above, address the need for either or both the ball component or trochanteral module component to be removed if replacement becomes necessary without extraction of the stem from the bone canal. Different size balls or trochanteral components could also be substituted should the surgeon decide that such revision is necessary after a period of time. These conventional devices also contemplate selecting from a variety of sizes of their components, in order to match the anatomy of a given patient as closely as possible within the inherent variability of the assembly.

However, the modular systems, notwithstanding the variability offered in their assemblage of specifically sized components, fail to provide an infinite variability within a give size range while creating an assembly of enhanced biomechanical strength. That is, the prior assemblies introduce torsional tresses at the junctures of their components which do not necessarily reflect a unitary construction. Moreover, a wide array of sizes must be kept in stock during surgery to match a patient's anatomy.

Therefore, there is a need for a prosthesis which relies upon an enhanced means of connecting its components together, while further providing infinite adjustability within a given size range, while forming an assembly which biomechanically functions as an integral structure.

SUMMARY OF THE INVENTION AND ADVANTAGES

According to the present invention, there is provided an implantable modular orthopedic prosthesis which consists of three components. A first component has an elongated stem with a free end, configured to be situated within the intramedullary canal of a patient's bone, and an opposite end having an articulating portion. A second component has another articulating portion operatively engageable with the articulating portion of the first component. A body includes an extruded channel through which the articulating portions are adjustably received. A radially flexible portion is disposed in the channel to pressure lock against an internal surface of the channel and articulating portions of the first and second components to arrest the first and second components and the body together in a fixed relative position as the articulating portions are engaged with one another.

In a preferred embodiment of the invention, the prosthesis is a modular hip, while in another preferred embodiment it is a modular knee, particularly, a tibial prosthesis. In a third embodiment, it is a modular shoulder.

In another preferred embodiment of the invention, a tensioning member urges the articulating portions together, causing the radially-expanding component to pressure-lock against the internal surface of the channel and affix the three components together. Moreover, it is further preferred that the radial-expansion take the form of a split collet mechanism.

In a further preferred embodiment of the invention, the articulating portions are complementary tapered connectors.

An advantage of the present invention is an improved mechanism for interlocking the components of a modular orthopedic prosthesis which, following implantation, functions as a unitary biomechanical structure.

Another advantage of the present invention is a prosthetic system which is easy to use and interoperatively adjustable to fit minute variations in a patient's given anatomy, while minimizing the inventory of component sizes needed on hand during surgery.

BRIEF DESCRIPTION OF THE DRAWINGS

Further objects and advantages of the invention will become apparent to one skilled in the art by resort to the following Drawings, taken in conjunction with the accompanying Detailed Description, with the reference numerals given in the text corresponding to similarly numbered structures in the Drawings, wherein:

FIG. 7 is a longitudinal sectional view of the prosthesis of FIG. 5, taken along the lines 25—25 of FIG. 6;

FIG. 8 is a perspective view of the hip prosthesis of FIG. 1, shown fully assembled with the stem component in its maximally extended position;

FIG. 13 is an exploded perspective view of the components of the invention embodied in a preferred modular hip prosthesis, with the expanding collet mechanism located on the neck;

FIG. 14 is a longitudinal sectional view of the prosthesis of FIG. 13, taken along the lines 14—14;

FIG. 19 is an exploded perspective view of the components of the invention embodied in a preferred modular tibial prosthesis, with the expanding collet mechanism located on the stem;

FIG. 20 is a longitudinal sectional view of the tibial prosthesis of FIG. 19, taken along the lines 20—20;

FIG. 29 is a side view of a humeral prosthesis in an assembled state;

FIG. 30 is a cross-sectional view taken along lines 30—30 of FIG. 29;

FIG. 31 is an exploded view of a further embodiment of the present invention;

FIG. 32 is a cross-sectional view taken along the longitudinal access of the embodiment shown in FIG. 1.

DETAILED DESCRIPTION OF THE INVENTION

Figure 1:
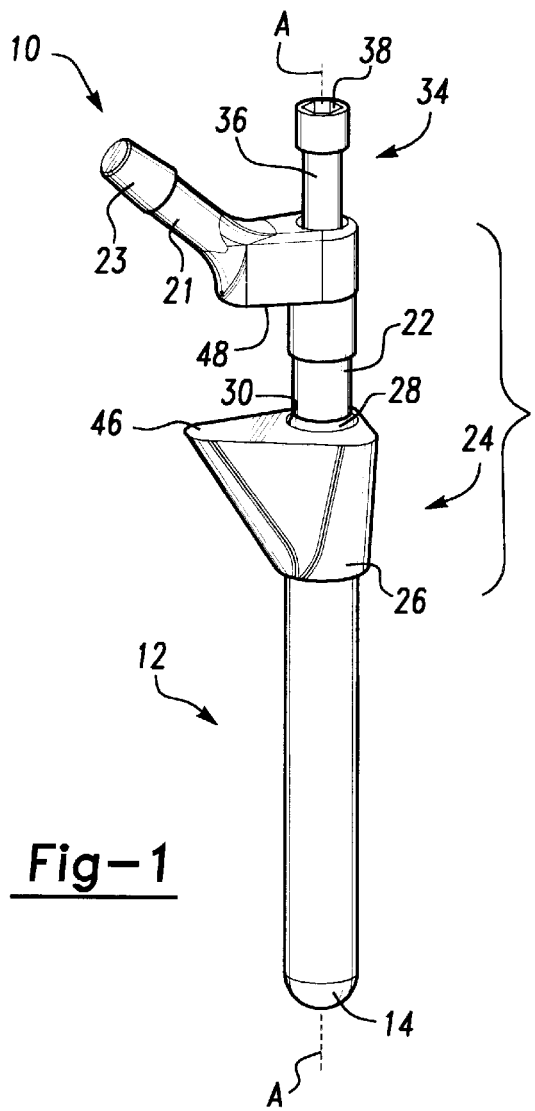
FIG. 1 is an exploded perspective view of the components of the invention embodied in a preferred modular hip prosthesis.
Figure 2:
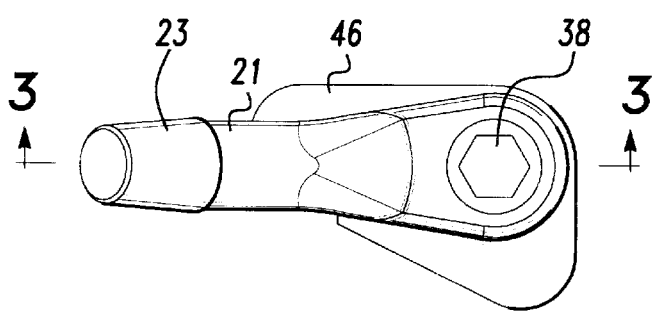
FIG. 2 is an external top view of the prosthesis of FIG. 1.
Figure 3:
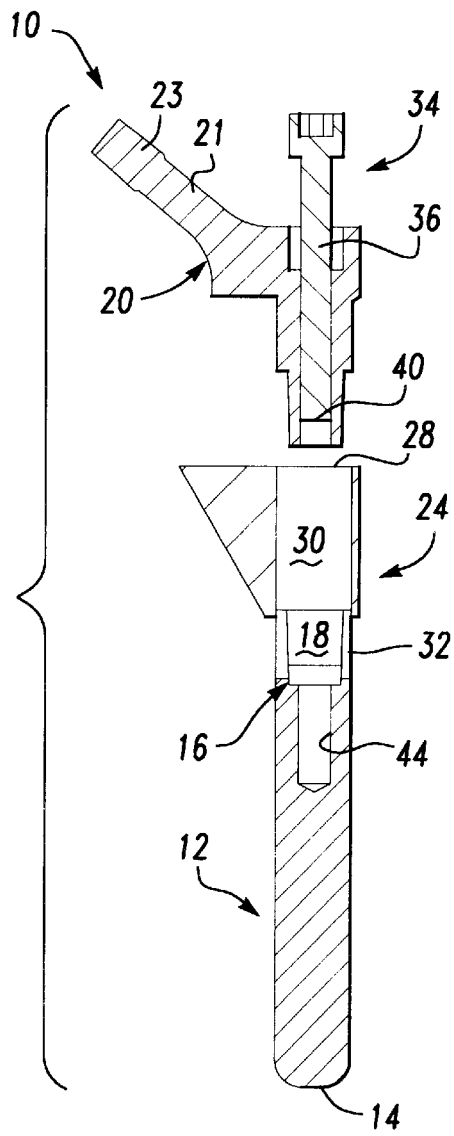
FIG. 3 is a longitudinal sectional view of the prosthesis of FIG. 2, taken along the lines 3—3.

Referring to one or more of the preferred embodiments of the present invention, as depicted in FIGS. 1–17, there is provided an implantable modular orthopedic prosthesis, in this case a hip prosthesis, generally shown at 10, which is comprised of multiple components.

A first component is an elongated stem, generally shown at 12, with a free distal end 14, configured to be situated within the intramedullary canal of a patient's bone (not shown), and an opposite end, generally indicated at 16, having an articulating portion, preferably a tapered connecting member, such as the female frusto-conical bore 18.

A second component is a neck, generally shown at 20, which has another articulating portion, preferably a complementary tapered connector such as the tapered post 22, which is matingly engageable with the tapered bore 18 of the stem 12.

A third component is a trochanteric module (sleeve), generally indicated at 24 having a contoured body 26 adapted for implantation into the resected proximal femur of a patient. A linearly-extruded channel 28 is formed through the module 24, along an axis A (FIG. 1) generally coincident with the longitudinal axis of the stem 12, with an internal surface 30.

The articulating portions 18,22 are adjustably received within the channel 28, such that the module 24 can be axially moved along axis A relative to stem 12 and neck 20 to adjust the distance between the module and the neck and stem, respectively. At least one of the components is radially-expandable, preferably by means of the expanding collet mechanism 32, to pressure lock against the internal surface 30 of the channel 28 in a selected position and arrest the first (stem 12), second (neck 20) and third (module 24) components together as the articulating portions, i.e., tapered bore 18 and post 22, are fully engaged with one another. Although the tapered bore 18 and collet 32 are shown in FIGS. 1–12 as being located on the stem 12, the location of these elements may be reversed so that they are on the neck, as will be described hereinafter with reference to FIGS. 13–17.

Referring again to FIGS. 1–17, the hip prosthesis 10 further comprises a tensioning member, generally indicated at 34, operatively connecting the stem 12 and neck 20, to urge the articulating tapered bore 18 and post 22 together and affix all three components 12, 20, 24 of the prosthesis 10 together in a desired relative conformation.

The tensioning member preferably consists of a locking bolt 34 having an elongated shaft 36 with a driven end 38 and a threaded end 40 which passes distally through an opening 42 formed in the neck 20, thence through the tapered bore 18 and post 22 to threadedly engage a tapped aperture 44 in the stem 12. Although not specifically described, the bolt 34 can alternatively be passed through an opening optionally formed in the distal end 14 of the stem 12 (not shown) and continuing proximally to engage a threaded aperture in the neck (not shown), as will be appreciated by those skilled in the art.

The linearly extruded channel 28 preferably has a circular cross section, e.g., a cylindrical bore, allowing infinitely variable rotational adjustment of the stem 12 and neck 20 relative to one another, and allowing proximal-distal adjustment of these components within the channel 28.

It will be appreciated by those skilled in the art that the channel 28 may alternatively have a polygonal cross section or a star shape (not shown) while the articulating portions could have corresponding shapes which would be respectively indexable relative to the channel in a finite selection of rotational alignments, rather than the infinite rotational adjustability afforded by the tapered connection described herein. Having a square shaped channel (not shown), for example, allows for four orthogonal relative rotations of the neck 20 and stem 12, while the multi-point star shape would allow for multiple rotations of the neck and stem. The linearly extruded cut of the channel 28 also allows for the independent insertion, rotation and removal of the stem 12 without removing the anatomically press fit trochanteric module 24, once implanted. Though inserting stem 12 from the proximal end of the neck has its advantages, inserting stem 12 from the distal direction proximally into the neck, prior to insertion into the femoral bone, allows for greater mechanical stability and variable design flexibility.

The body 26 of trochanteric module 24 has a proximal shoulder 46 which abuts a stop 48 formed on the neck 20 limiting the range of axially adjustable telescoping movement of the surrounding trochanteric module 24 relative to the neck and stem 12 prior to full engagement of the articulating bore 18 and post 22 by tightening of the bolt 34. Module 24 can have rounded triangular cross section, adjacent the proximal shoulder 46, the area of which reduces distally, shown e.g., in FIGS. 10–11, although it can have other shapes as would be known by those skilled in the art. The neck 20 is equipped with an integral, angulated member 21 with a further tapered post 23 for attachment of a conventional ball (not shown).

Figure 4:
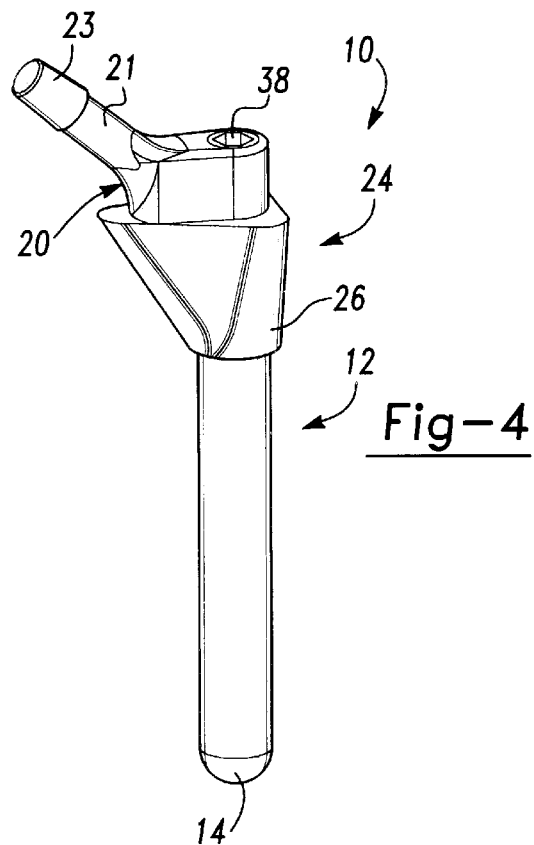
FIG. 4 is a perspective view of the hip prosthesis of FIG. 1, shown fully assembled with the stem component in its minimally extended position.
Figure 5:
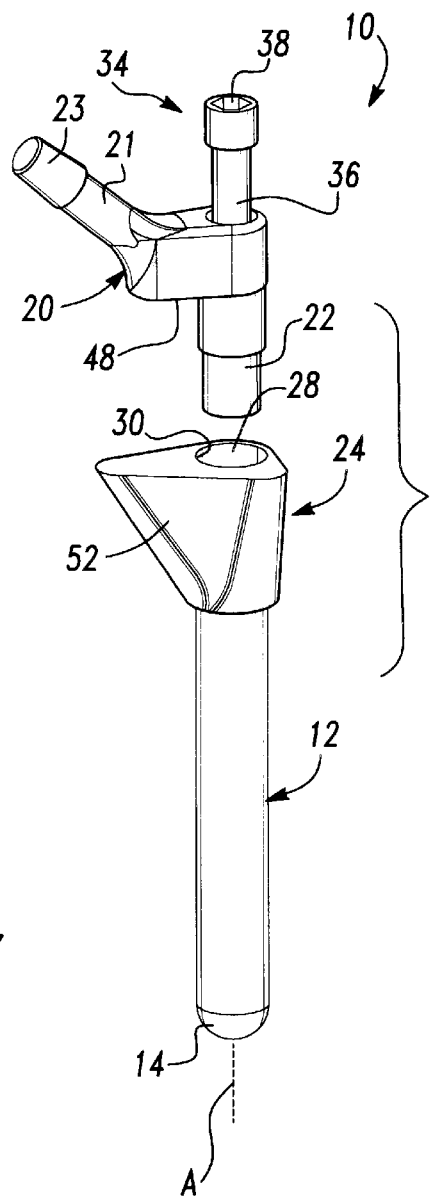
FIG. 5 is an exploded perspective view of the components of the invention embodied in a preferred modular hip prosthesis.
Figure 6:
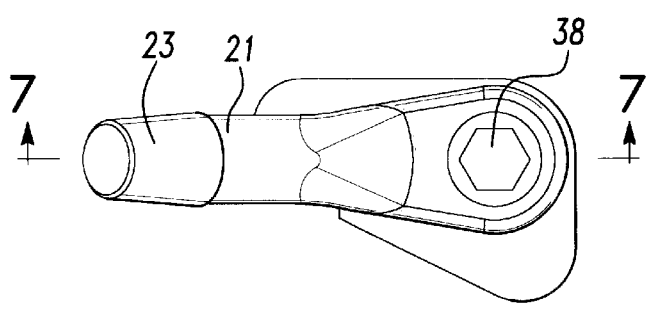
FIG. 6 is an external top view of the prosthesis of FIG. 5.

In FIG. 4, the prosthesis 10 is shown with the stem 12 in its non-extended position, that is, the shoulder 46 abuts the stop 48 with the components 12,20,24 affixed together. For aesthetic purposes, the collet 32 is fully constrained within the channel 28, as shown in FIG. 4. The collet 32 is actuated within channel 28 to pressure-lock against internal surface 30 in a selected location such that the shoulder 46 is axially spaced from the distal stop 48 as shown in FIG. 8. Thus, a patient can be fitted with a fixed size of prosthetic components, then the sized components adapted to either increase (FIG. 8) or decrease (FIG. 4) the effective length of the stem 12 depending upon the patient's anatomy, without resorting to a more complex assortment of intermediate sizes of trial implants and prosthetic components.

Figure 9:
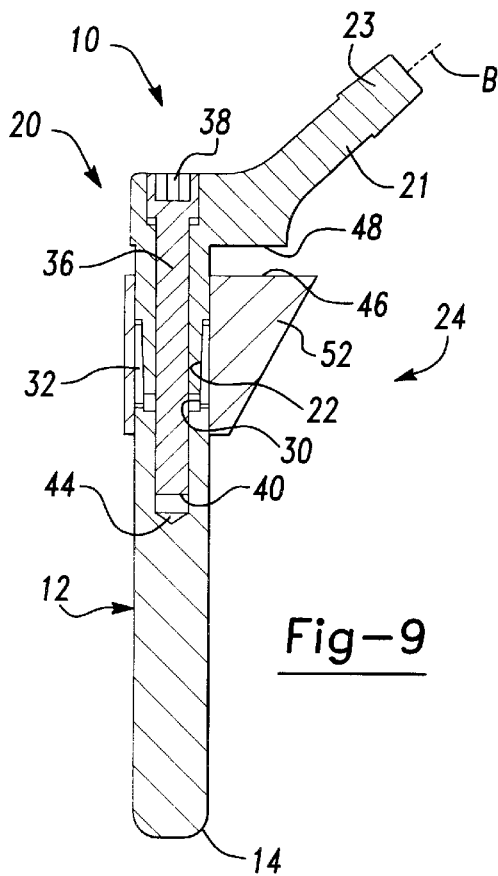
FIG. 9 is a longitudinal sectional view of the prosthesis of FIG. 8, taken along the lines 9—9.
Figure 10:
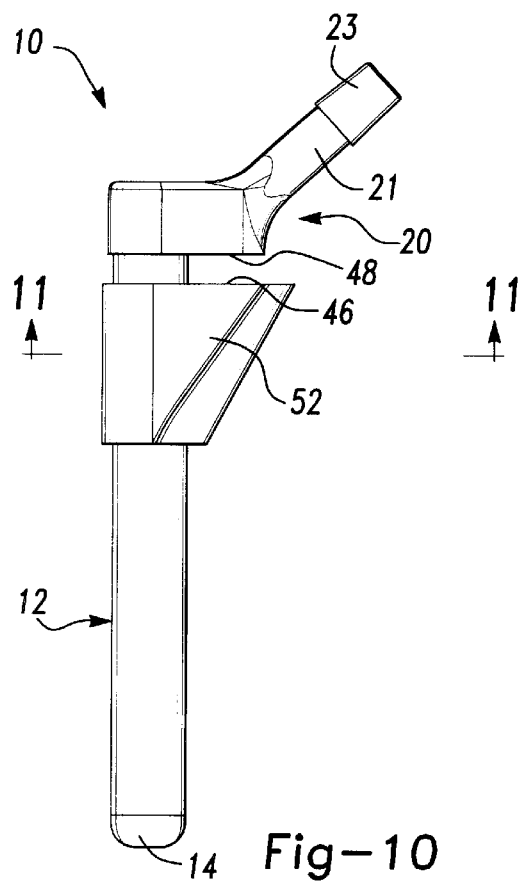
FIG. 10 is a longitudinal sectional view of the prosthesis of FIG. 8, taken along the lines 9—9.
Figure 11:
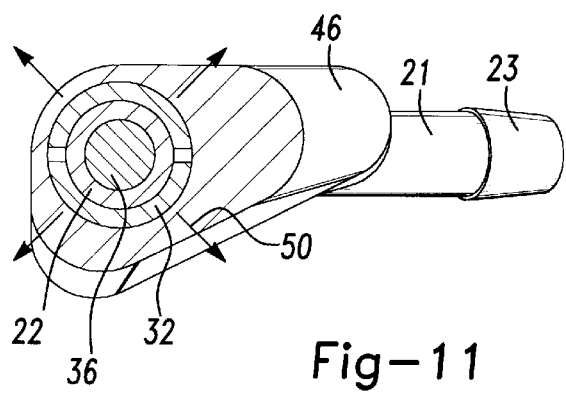
FIG. 11 is a transverse sectional view of the hip prosthesis of FIG. 8, taken along the lines 11—11, showing the preferred expanded collet mechanism of the invention located on the stem.
Figure 15:
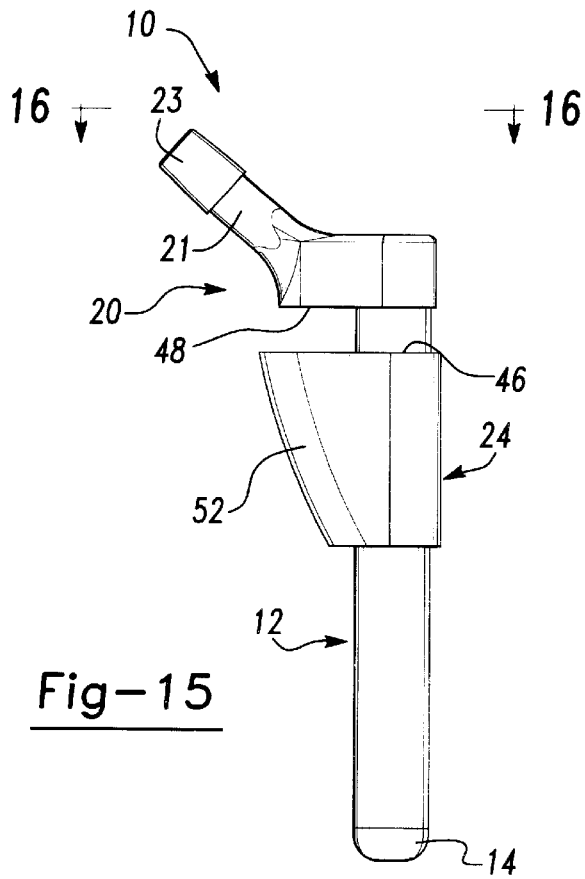
FIG. 15 is a perspective view of the hip prosthesis of FIG. 13, shown fully assembled with the stem component in its maximally-extended position.

Referring to FIGS. 9–11, the mechanism deployed via collet 32 is depicted. FIG. 11 shows the collet 32 expanded radially against the internal surface 30 in the direction of arrows 50, in the manner described above, i.e., by actuation of the locking bolt 34.

Figure 12:
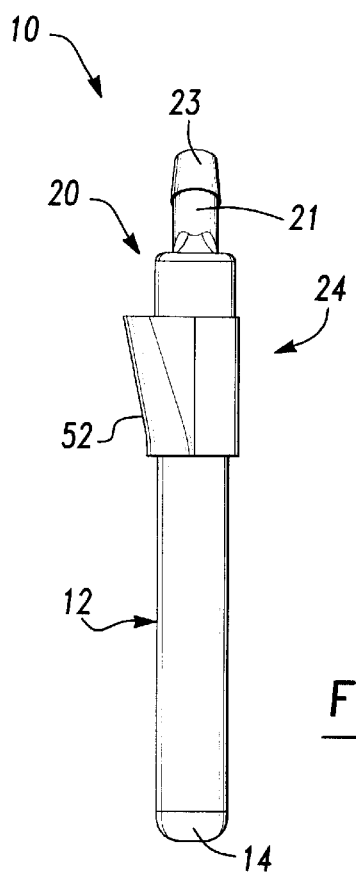
FIG. 12 is a side view of the preferred hip prosthesis of the invention, shown in an assembled state with the stem in its minimally-extended position and the trochanteric module rotated to an alternative conformation.

In FIG. 12, a hip prosthesis 10 of the present invention is shown having the trochanteric module 24 rotationally adjusted so that the portion of the body 26 which forms a transverse triangular faceted shaped member 52 forms a complex angle with the axis B of the ball post 23 and the axis A of the stem 12.

FIGS. 13–17 show a prosthesis 10 with an alternative juxtaposition of the collet 32 and tapered bore 18 situated on the neck 20 rather than stem 12 and the tapered post 22 located on the proximal articulating portion of the stem 12. The prosthesis 10, like the embodiment of FIGS. 1–12, may be assembled either with stem 12 in a maximally-extended (FIGS. 15–16) or minimally-extended (FIG. 17) conformation.

Figure 16:
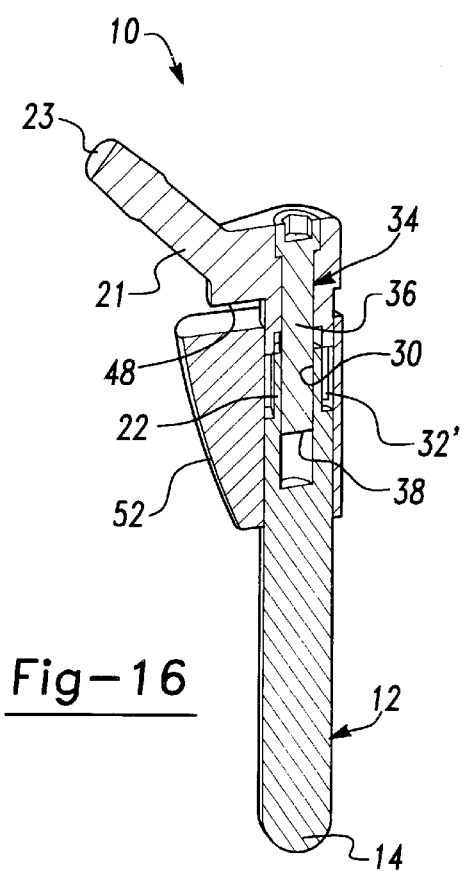
FIG. 16 is a longitudinal sectional view of the prosthesis of FIG. 15, taken along the lines 16—16.
Figure 17:
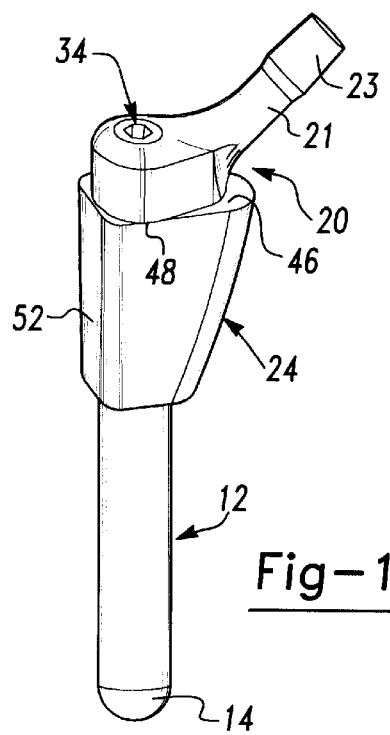
FIG. 17 is a perspective view of the hip prosthesis of FIG. 13, shown fully assembled with the stem component in its minimally-extended position.

More specifically referring to FIGS. 16 and 17, the collet 32' is shown slotted. The collet 32' includes maximally extending slots 33 defining fingers 35 which are radially expandable. Upon insertion and tightening of the bolt 34, the stem is drawn proximally and the fingers 35 are forced radially outwardly so as to lock against the inner surface 30 of the member 52. This is an alternative configuration to the typical tapered connection described above. Of course, those skilled in the art can reverse the configuration so that such fingers 35 are inwardly-radially flexed to produce a locking grip.

Figure 18:
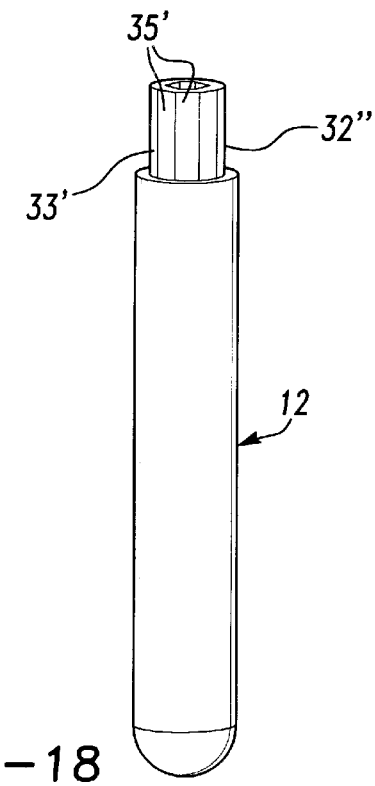
FIG. 18 is a longitudinal sectional view of a stem including a slotted proximal portion.
Figure 21:
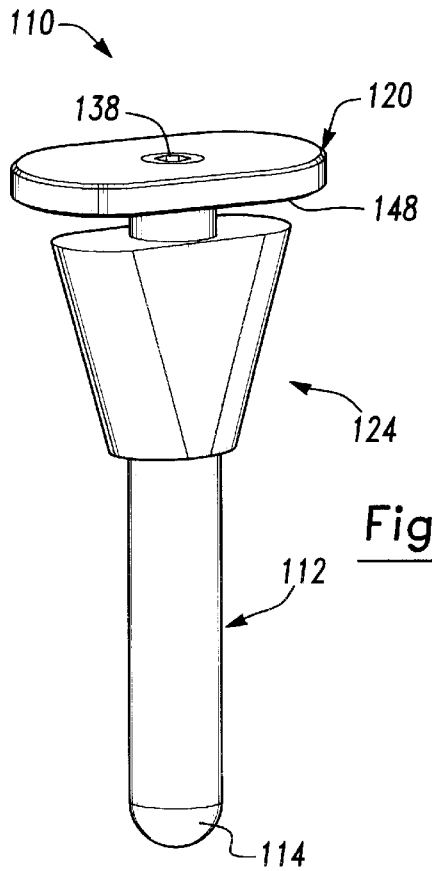
FIG. 21 is a perspective view of the tibial prosthesis of FIG. 19, shown fully assembled with the stem component in its maximally-extended position.
Figure 22:
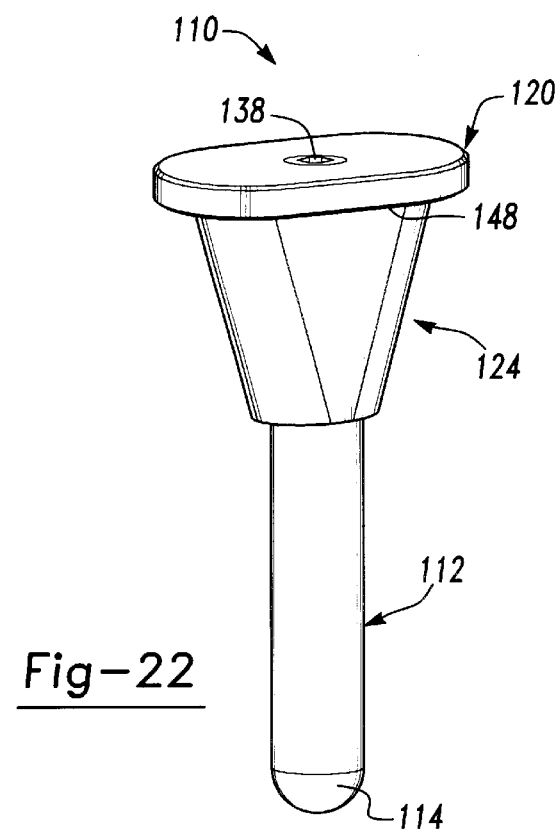
FIG. 22 is a perspective view of the tibial prosthesis of FIG. 19, shown fully assembled with the stem component in its minimally-extended position.
Figure 23:
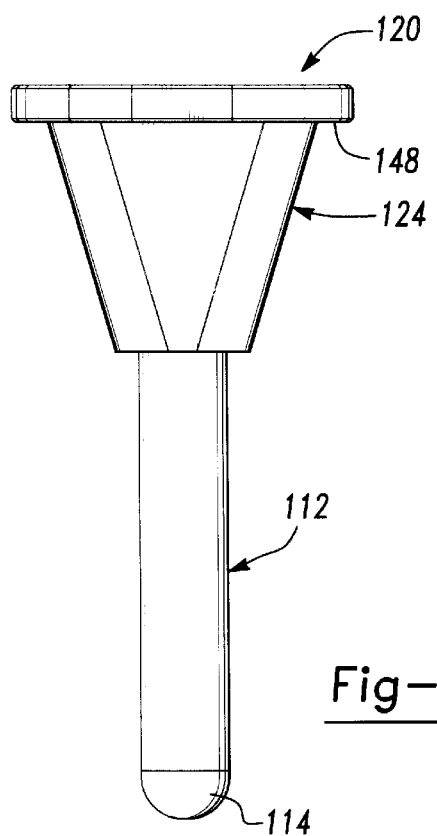
FIG. 23 is a side view of the prosthesis of FIG. 19, shown in an assembled state with the stem in its minimally-extended position and its transition module proximally abutting the distal surface of the tray.
Figure 24:
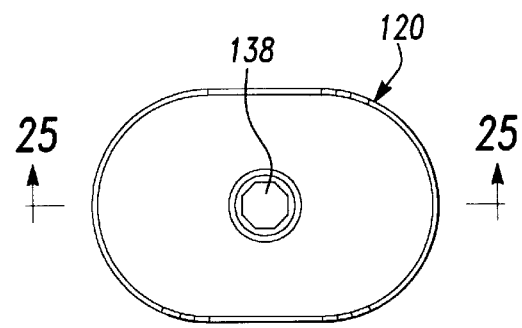
FIG. 24 is an external top view of the tibial prosthesis of FIG. 23.
Figure 25:
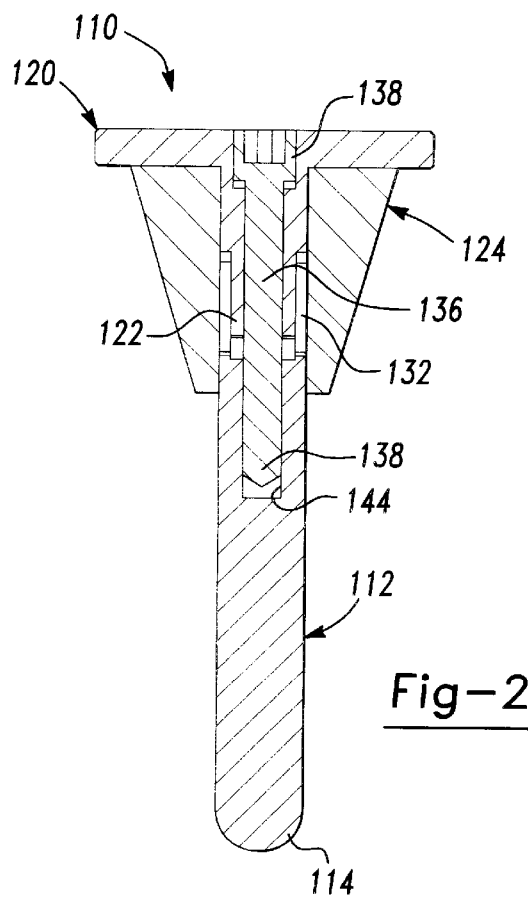
FIG. 25 is a longitudinal sectional view of the tibial prosthesis of FIG. 23, taken along the lines 25—25 of FIG. 24.
Figure 26:
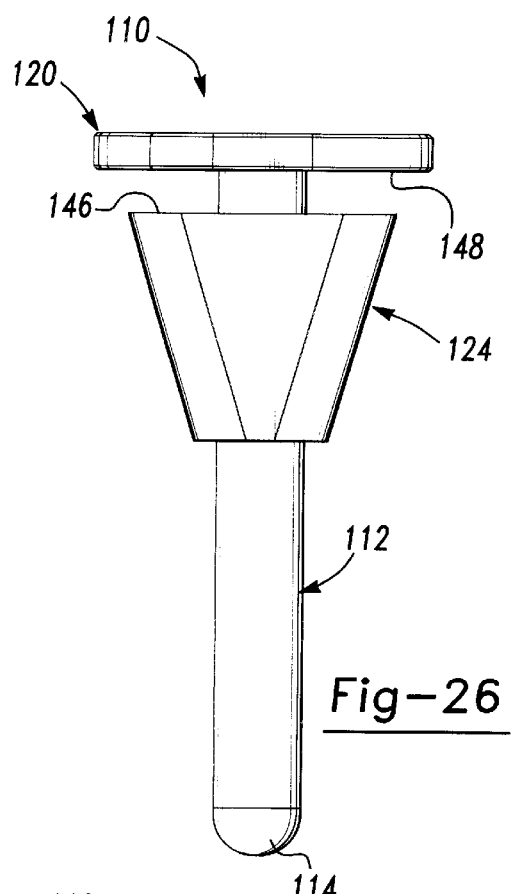
FIG. 26 is a side view of the prosthesis of FIG. 19, shown in an assembled state with the stem in its maximally-extended position and its transition module spaced from the distal surface of the tray.
Figure 27:
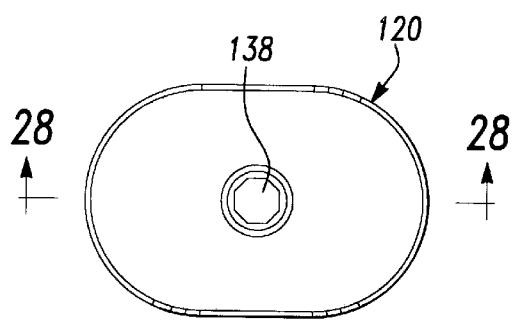
FIG. 27 is an external top view of the tibial prosthesis of FIG. 26.
Figure 28:
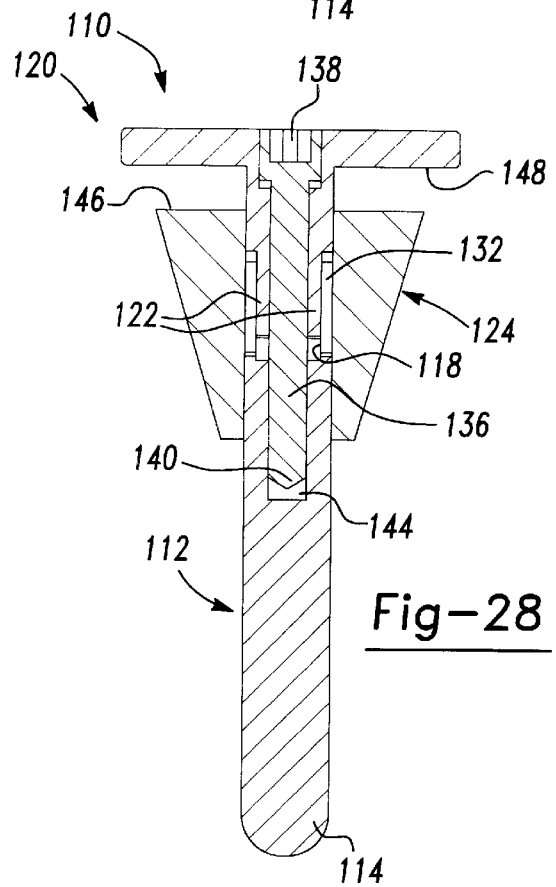
FIG. 28 is a longitudinal sectional view of the tibial prosthesis of FIG. 26, taken along the lines 28—28 of FIG. 27.

An alternative embodiment is shown in FIG. 18 wherein the stem 12 includes the radial 14 expandable collet portion 32". The collet portion 32" includes slots 33' defining radially expandable fingers 35'. In this embodiment, insertion of the bolt 34 (not shown) will expand the fingers 35' creating the locking force against the inner surface 30 of the member 52.

Traditional fixation mechanisms for modular implants typically use tapered connections. The taper is designed to withstand compressive forces and rotational torque, but is not particularly well suited for tension forces and bending moments. It can be shown that bending moments induced on a tapered connection, where the independent components have dissimilar moments of inertia, can cause surface micro motion at the connection and hence wear, wear debris and eventual failure of the connection. The fully contained radial expansion mechanism described herein, with reference to collet 32, transfers the bending moments induced on the implanted prosthesis 10, due to day-to-day activities, away from the articulating portions which connect the stem 12 and neck 20 components, toward the strongest portion of the prosthetic joint. Thus the expansion mechanism experiences much less stress than the interface of traditional tapered connections for modular hip stems.

Independent, infinite rotational variability of the stem 12 to fit the patient advantageously allows for the rotational control of distal bends and coronal slots used commonly on distal stems (not shown) for a better match to the femoral anatomy and reduction in patient pain caused by point stresses against the medullary canal wall of the femur.

Separate options are available allowing for the cost effective use on the trochanteric module 24 of the many popular coatings such as HA, heavy bead blast, or porous coating without the complication of protecting the tapered post.

The surgical procedure for preparing the patient to be implanted with the prosthesis 10 can be chosen from a variety of generally recognized methods and instrumentation, however, an example of a suitable technique is given in the aforementioned U.S. Pat. No. 5,201,882 to Paxson, the entire disclosure of which is expressly incorporated by reference herein and relied upon.

The prosthesis 10 is a modular connection system for use in total joint arthroplasty. Therefore, the rotational and linear extension mechanism of the invention can readily be applied to knee, shoulder and hip joint replacement components each having similar characteristics and functional advantages as it relates to adjustable bone fixation. A tibial prosthesis for use in total knee arthroplasty and a shoulder prosthesis will be described below.

Referring to FIGS. 19–28, an implantable modular tibial prosthesis 110 is depicted, with an elongated stem 112 having a free distal end 114, configured to be situated within the intramedullary canal of a patient's bone, and an opposite end 116 having preferably a tapered bore 118. A tibial tray 120, having another articulating portion in the form of a tapered post 122, is matingly engageable with the tapered bore 118 of the stem 112, for attaching the tray 120 and stem 112 together in a selected fixed rotational conformation. A transition module, generally shown at 24, has a body 126 with a linearly-extruded channel 128 having an internal surface 130, through which the articulating tapered bore 118 and post 122 of the stem 112 and tray 120, respectively, are telescopically received. Preferably, the stem 112 is radially-expandable by means of an expanding collet mechanism 132 to pressure lock against the internal surface 130 of the channel 128 in a selected location to arrest the stem 112, tray 120 and transition module 124 together in a fixed axial and rotational relationship as the mating articulating connectors 118, 122 are fully engaged with one another.

A tensioning member, such as the locking bolt 134, operatively connects the stem 112 and tray 120, to urge the tapered bore 118 and post 122 fully together to affix the tray, stem and transition module together in a desired relative conformation.

The locking bolt 134 has an elongated shaft 136 having a driven end 138 and a threaded end 140 which passes through an opening 142 formed in the tray 120 to threadedly engage a tapped aperture 144 in the stem 112.

Although the stem 112 of prosthesis 110 has a tapered bore 118 and the neck 120 has the complementary tapered post 122, respectively, these elements can be reversed (not shown), similar to the juxtaposition described above in FIGS. 1–12 versus FIGS. 13–17, for the hip prosthesis 10. That is, and although not shown in the Drawings, the tray 120 could have the radially expandable collet and tapered bore, rather than having them on the stem 112 to pressure lock against the internal surface of the channel.

Channel 128 formed in the transition module 124 preferably has a circular cross section, e.g., a cylindrical bore, allowing infinitely variable rotational adjustment of the tray and stem relative to one another, and allowing axial adjustment of the transition module relative to the engaged tray and stem.

While not specifically shown in the Drawings, it will be appreciated from the foregoing discussion that the channel 128 could have a polygonal cross section and the articulating portions could have corresponding shapes which are respectively indexable relative to the channel in a finite selection of rotational alignments.

Referring to FIGS. 17–28, a shoulder 146 is formed on the transition module 124 which abuts a stop 148 formed on the tray 120, limiting the range of axially adjustable telescoping movement of the transition module relative to the tray and stem 112 prior to full engagement of the articulating portions 118, 122 thereof. Prior to tightening of the tapered bore 118 and post 122 together by turning bolt 134, the transition module 124 can be slid in either the proximal direction to decrease the effective length of the stem 112 by abutment of shoulder 146 with stop 148 (FIGS. 21–24), or distally to increase the stem length (FIGS. 20 and 25–27) leaving the shoulder 146 spaced from stop 148.

A variety of techniques are generally recognized as acceptable for the preparation of the patient's bone to receive the tibial prosthesis of the present invention, these being well known to those skilled in the art.

An implantable modular humeral prosthesis 210 is generally shown in FIGS. 29 and 30. The prosthesis 210 is constructed in a similar manner in regard to the present invention as the hip prosthesis depicted in FIGS. 1–12. That is, the prosthesis 210 includes a stem 212, a neck portion 220 and a sleeve 224 disposed therebetween. Referring specifically to FIG. 30, the neck portion includes an articulating tapered connecting member in the form of a frustalconnical bore 218. The stem 212 includes a complementary tapered connector in the form of a tapered post 222. As with the embodiments described above, this configuration can be reversed between the neck portion 220 and stem 212; that is, the neck portion 220 can include a tapered connector in the form of a tapered post and the stem 212 can include the tapered connector in the form of a frusto-conical bore 218.

The neck portion 220 is configured to include a surface 226 for receiving an articulating member therein for articulation with a shoulder socket.

A connecting member in the form of a bolt 234 interconnects the three components 212,220,224 together in a manner as described above.

Figure 33:
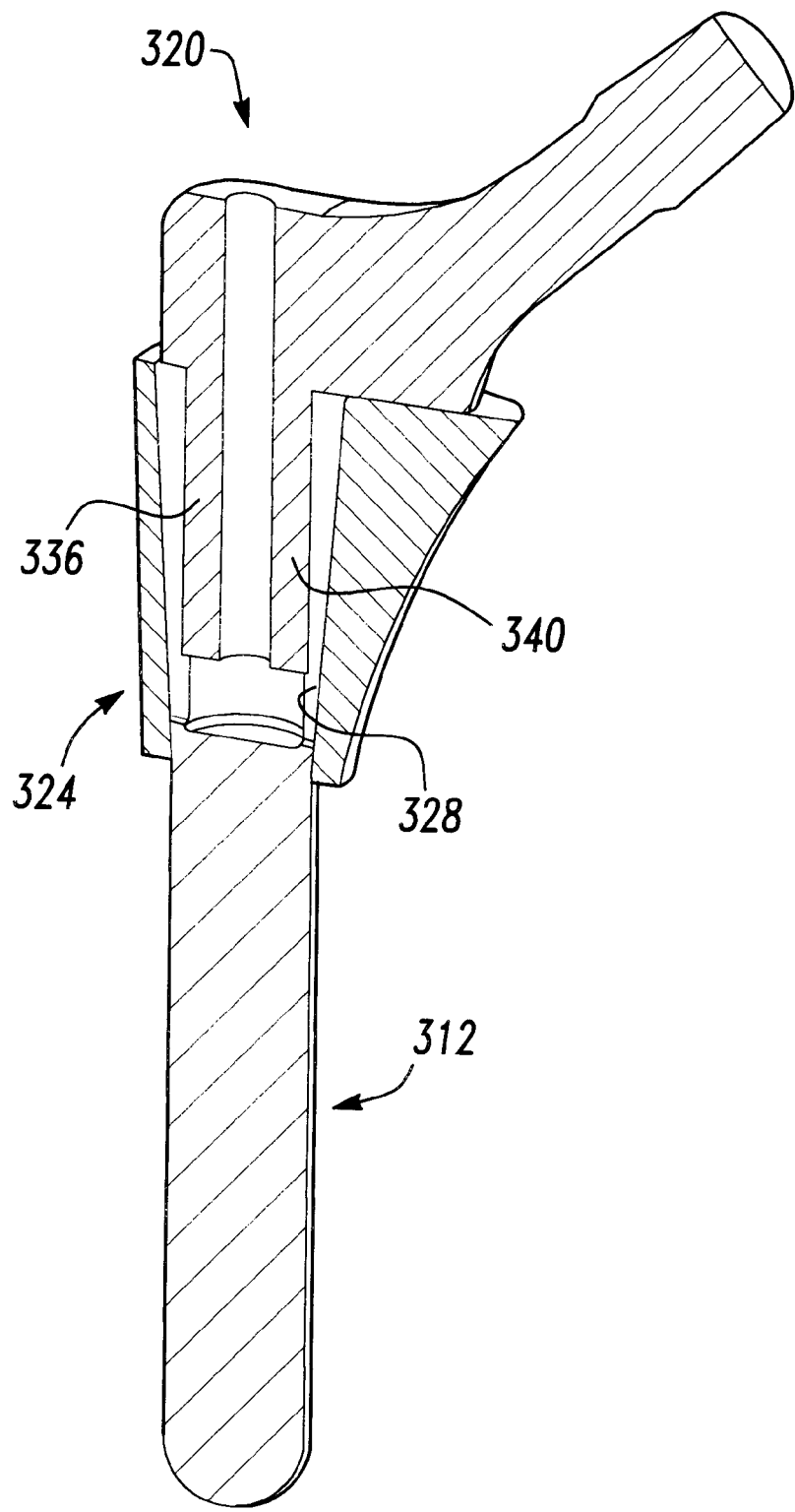
FIG. 33 is an assembled view in cross section of the embodiment shown in FIG. 31.

A further embodiment of the present invention is shown in FIGS. 31–33. In this embodiment, the stem 312 includes a free distal end 314 for insertion within the intramedullary canal of a patient's bone (not shown) and an opposite end generally indicated at 316 in the form of a split collet 332. The split collet 332 comprises a plurality of slots 333 defining a plurality of fingers 335 which are radially expandable. A sleeve generally shown at 324 includes a tapered passageway 328 having an internal surface 330. A neck member 320 includes a threaded bolt-type portion 336 extending integrally therefrom. The collet portion 316 of the stem 312 includes an internal threaded surface 340 for threadingly engaging the bolt 336.

In use, the contraction mechanism of this embodiment is designed to allow the split collet 316 on the proximal end of the stem 312 to expand against the inner surface 328 of the sleeve 324 as the bolt portion 336 is engaged within the threaded bore 340 of the collet 316. The threaded engagement allows for infinite variability of the relationship between the neck portion 320 and the remainder of the assembly. This "three-piece" assembly does not require the additional screw member of the aforementioned assemblies. Additionally, the sleeve 324 is disposed over the collet portion 316 by sliding the sleeve 324 from the distal end 314 up the stem 316 and eventually over the collet portion 316.

In view of the above, the present invention can be incorporated to various prosthetic assemblies for hip, shoulder, and knee replacement.

While applicant has described certain specific embodiments of the invention for illustrative purposes, various modifications will be apparent to those skilled in the art which do not constitute departures from the spirit and scope of the invention as defined in the appended claims.

The invention has been described in an illustrative manner, and it is to be understood the terminology used is intended to be in the nature of description rather than limitation. Obviously, many modifications and variations of the present invention are possible in light of the above teachings.

What is claimed is:

1. An implantable modular orthopedic prosthesis assembly comprising:
    a first component having an elongated stem with a free end, configured to be situated within the intramedullary canal of a patient's bone, and an opposite end having an articulating portion;
    a second component having another articulating portion; operatively engageable with the articulating portion of the first component;
    a third component having a body with a channel through which the articulating portions are adjustably received; and
    a radially flexible mechanism, associated with at least one of the first and second components, wherein the radially flexible mechanism is adapted to pressure lock against the channel to arrest the first, second and third components together in a fixed relative position as the articulating portions are fully engaged.

2. The prosthesis of claim 1 further comprising a tensioning member, operatively connecting the first and second components, to urge the articulating portions together and lock all three components of the prosthesis together in a desired relative configuration.

3. The prosthesis of claim 2 wherein the tensioning member further comprises an elongated shaft having a driven end and a threaded end which passes through an opening formed in the second component to threadedly engage a tapped aperture in the first component.

4. The prosthesis of claim 3 wherein the tensioning member further comprises a separate locking bolt.

5. The prosthesis of claim 1 wherein the articulating portions of the first and second components, respectively, further comprise complementary tapered connectors.

6. The prosthesis of claim 5 wherein the articulating portion of the a first component has a tapered bore and the articulating portion of the second component has a corresponding tapered post, respectively, for mating engagement with one another.

7. The prosthesis of claim 1 wherein the channel formed in the third component further comprises a cylindrical bore, allowing infinitely variable rotational adjustment of the first and second components relative to one another, and allowing axial adjustment of the engaged first and second components within the cylindrical bore.

8. The prosthesis of claim 1 wherein the first component is radially expandable to pressure lock against the internal surface of the channel.

9. The prosthesis of claim 1 wherein the second component is radially expandable to pressure lock against the internal surface of the channel.

10. The prosthesis of claim 1 further comprising a split collet, which is formed on the radially expandable component and axially constrained within the channel to pressure lock against the internal surface of the channel to affix the three components together.

11. The prosthesis of claim 10 wherein said split collet is said opposite end of said stem.

12. The prosthesis of claim 10 wherein said split collet is on a proximal portion of said first component.

13. The prosthesis of claim 1 wherein the channel has a polygonal cross section and the articulating portions have corresponding shapes which are respectively indexable relative to the channel in a finite selection of rotational alignments.

14. The prosthesis of claim 1 further comprising a shoulder formed on the third component which abuts a stop formed on the second component, limiting the range of axially adjustable telescoping movement of the third component relative to the first and second components prior to full engagement of the articulating portions thereof.

15. An implantable modular orthopedic prosthesis comprising:
    a first component having an elongated stem with a free end, configured to be situated within the intramedullary canal of a patient's bone, and an opposite end having an articulable tapered bore;
    a second component having a tapered post matingly engageable with the tapered bore formed in the first component, for attaching the first and second components together in a selected fixed rotational conformation; and
    a third component having a body with a linearly-extruded cylindrical bore through which the articulable tapered bore and tapered post are telescopically received, wherein the second component has a radially-expandable split collet to pressure lock against the internal surface of the cylindrical bore in a selected axial location to arrest the first, second and third components together in a fixed axial and rotational relationship as the mating tapered post and tapered bore are fully engaged with one another.

16. The prosthesis of claim 15 wherein the articulating portions of the stem and neck respectively, further comprise complementary tapered connecting members.

17. The prosthesis of claim 16 wherein the articulating portion of the stem has a tapered bore and the articulating portion of the neck has a complementary tapered post, respectively.

18. The prosthesis of claim 15 wherein the stem is radially expandable to pressure lock against the channel.

19. The prosthesis of claim 15 wherein the neck is radially expandable to pressure lock against the internal surface of the channel.

20. An implantable modular hip prosthesis comprising:
- an elongated stem with a free end, configured to be situated within the intramedullary canal of a patient's bone, and an opposite end having an articulating tapered bore;
- a neck having a tapered post matingly engageable with the tapered bore formed in the stem for attaching the neck and stem together in a selected fixed rotational conformation; and
- a trocanteric module having a body with a linearly-extruded cylindrical bore through which the articulating tapered bore and tapered post are telescopically received, wherein the neck has a radially-expandable split collet to pressure lock against the internal surface of the cylindrical bore in a selected axial location to arrest the stem, neck and trocanteric module together in a fixed axial and rotational relationship as the mating tapered post and tapered bore are fully engaged with one another.

21. An implantable modular knee prosthesis comprising:
- an elongated stem with a free end, configured to be situated within the intramedullary canal of a patient's bone, and an opposite end having an articulating portion;
- a tibial tray having another articulating portion matingly engageable with the articulating portion of the stem, for attaching the tray and stem together in a selected fixed rotational conformation; and
- a transition module having a body with a proximal shoulder and a linearly-extruded channel through which the articulating portions of the tray and stem are telescopically received, wherein at least one of the tray and stem is radially-expandable to pressure lock against the internal surface of the channel in a selected location to arrest the tray, stem and transition module together in a fixed axial and rotational relationship as the mating articulating portions are fully engaged with one another.

22. The prosthesis of claim 21 further comprising a tensioning member, operatively connecting the tray and stem, to urge the articulating portions together to affix the tray, stem and transition module together in a desired relative conformation.

23. The prosthesis of claim 22 wherein the tensioning member further comprises an elongated shaft having a driven end and a threaded end which passes through an opening formed in the tray to threadedly engage the stem.

24. The prosthesis of claim 23 wherein the tensioning member further comprises a locking bolt which threadedly engages a tapped aperture in the stem.

25. The prosthesis of claim 21 wherein the articulating portions of the stem and tray, respectively, further comprise complementary tapered connecting members.

26. The prosthesis of claim 25 wherein the articulating portion of the stem has a tapered bore and the articulating portion of the neck has a complementary tapered post, respectively.

27. The prosthesis of claim 21 wherein the channel formed in the transition module further comprises a cylindrical bore, allowing infinitely variable rotational adjustment of the tray and stem relative to one another, and allowing axial adjustment of the transition module relative to the engaged tray and stem.

28. The prosthesis of claim 21 wherein a proximal portion of the stem is radially expandable to pressure lock against the internal surface of the channel.

29. The prosthesis of claim 21 wherein a distal portion of the tray is radially expandable to pressure lock against the internal surface of the channel.

30. The prosthesis of claim 21 further comprising a split collet, which is formed on either of the radially expandable stem and tray and axially constrained within the channel to pressure lock against an internal surface of the channel and affix the stem, tray and transition module together.

31. The prosthesis of claim 21 wherein the channel has a polygonal cross section and the articulating portions have corresponding shapes which are respectively indexable relative to the channel in a finite selection of rotational alignments.

32. The prosthesis of claim 21 further comprising a shoulder formed on the transition module which abuts a stop formed on the tray, limiting the range of axially adjustable telescoping movement of the transition module relative to the tray and stem prior to full engagement of the articulating portions thereof.

33. An implantable modular tibia prosthesis comprising:
- an elongated stem with a free end, configured to be situated within the intramedullary canal of a patient's bone, and an opposite end having an articulating tapered bore;
- a tibial tray having a tapered post matingly engageable with the tapered bore formed in the stem for connecting the tray and stem together in a selected fixed rotational conformation;
- a transition module having a body with a linearly-extruded cylindrical bore through which the articulating tapered bore and post are telescopically received, wherein the stem has a radially-expandable split collet to pressure lock against the internal surface of the cylindrical bore in a selected axial location to arrest the stem, tray and transition module together in a fixed axial and rotational relationship as the mating tapered members are fully engaged with one another.

34. An implantable humeral prosthesis comprising a stem including a free end configured to be situated within the intermediary canal of a patient's humerus and an opposite end having an articulating portion;
- a neck member including a second articulating portion matingly engagable with said first articulating portion of said stem; and
- a sleeve member having a linearly extruded channel through which said articulating portions are adjustably received, at least one of said stem and neck portions being radially expandable to pressure lock against a surface of said channel and arrest said stem, neck and sleeve portions together in a fixed relative position.

35. An implantable modular orthopedic prosthesis assembly comprising:
- a first component having an elongated stem with a free end configured to be situated within the intramedullary canal of a patient's bone, and an opposite end having an articulating portion;
- a second component having another articulating portion operatively engageable with the articulating portion of the first component;
- a body having an extruded channel through which the articulating portions are adjustably received; and wherein at least one of the first and second components includes a radially flexible portion to pressure lock against an internal surface of the extruded channel and articulating portions of said first and second components to arrest the first and second components and body together in a fixed relative position as the articulating portions are engaged with one another.

36. An implantable modular orthopedic prosthesis assembly as in claim 35 wherein said second component includes integral connecting means for connecting said first component to said second component and said body.

37. An implantable modular orthopedic prosthesis assembly as in claim 36 wherein said integral connecting means includes a serrated rod portion extruding from and integral with said second portion, said first component including a serrated bore for receiving engagement with said rod portion.

38. An implantable modular orthopedic prosthesis assembly as in claim 37 wherein said first component includes a split collet defining said radially flexible integral therewith including said bore, said rod expanding said collet upon engagement therewith to force said collet against said extruded channel to lock said first and second components and said body together.

39. An implantable modular orthopedic prosthesis assembly as in claim 35 wherein said assembly includes a third component including said body.

* * * * *